(12) United States Patent
Longo et al.

(10) Patent No.: US 9,445,929 B2
(45) Date of Patent: Sep. 20, 2016

(54) DELIVERY DEVICE AND METHOD OF DELIVERY

(71) Applicant: Intact Vascular, Inc., Wayne, PA (US)

(72) Inventors: Michael Longo, Glenmoore, PA (US); Douglas Evans, Downingtown, PA (US); William James Harrison, Signal Mountain, TN (US)

(73) Assignee: Intact Vascular, Inc., Wayne, PA (US)

( * ) Notice: Subject to any disclaimer, the term of this patent is extended or adjusted under 35 U.S.C. 154(b) by 0 days.

(21) Appl. No.: 14/935,154

(22) Filed: Nov. 6, 2015

(65) Prior Publication Data

US 2016/0220401 A1    Aug. 4, 2016

Related U.S. Application Data

(63) Continuation of application No. 14/656,462, filed on Mar. 12, 2015.

(60) Provisional application No. 62/109,534, filed on Jan. 29, 2015.

(51) Int. Cl.

| | |
|---|---|
| *A61F 2/06* | (2013.01) |
| *A61F 2/966* | (2013.01) |
| *A61F 2/86* | (2013.01) |
| *A61F 2/962* | (2013.01) |

(Continued)

(52) U.S. Cl.

CPC ............... *A61F 2/966* (2013.01); *A61F 2/86* (2013.01); *A61F 2/962* (2013.01); *A61F 2002/826* (2013.01); *A61F 2002/9517* (2013.01); *A61F 2002/9665* (2013.01); *A61F 2250/0019* (2013.01); *A61F 2250/0039* (2013.01); *A61F 2250/0098* (2013.01)

(58) Field of Classification Search

CPC .......... A61F 2/966; A61F 2/958; A61F 2/86; A61F 2002/9517; A61F 2250/0098; A61F 2002/826

See application file for complete search history.

(56) References Cited

U.S. PATENT DOCUMENTS

| | | |
|---|---|---|
| 3,051,172 A | 8/1962 | Bruchhaus |
| 4,921,484 A | 5/1990 | Hillstead |
| 4,994,065 A | 2/1991 | Gibbs et al. |

(Continued)

FOREIGN PATENT DOCUMENTS

| | | |
|---|---|---|
| EP | 0714640 | 6/1996 |
| EP | 1393766 A1 | 3/2004 |

(Continued)

*Primary Examiner* — Richard Louis (74) *Attorney, Agent, or Firm* — Knobbe, Martens Olson & Bear, LLP (57) ABSTRACT

A delivery device can provide sequential delivery of a plurality of intraluminal devices or tacks held in a compressed state on the delivery device. Delivery platforms on the delivery device can hold a tack in a compressed position and have a unique shape, such as a non-constant outer diameter, an hourglass shape, a tapered proximal half, ridges, dimples, etc. This unique shape can be positioned between annular pusher bands that may also be radiopaque markers. In some embodiments, the unique shape is provided by a sleeve of flexible material with the unique shape surrounding a harder inner shaft. Further, the annular pusher bands can be made of wire or sections of material to increase flexibility while remaining radiopacity. A tack deployment method can include alignment of radiopaque markers on the outer sheath and the tack to be deployed prior to deployment.

25 Claims, 6 Drawing Sheets

(51) Int. Cl.
*A61F 2/82* (2013.01)
*A61F 2/95* (2013.01)

(56) References Cited

U.S. PATENT DOCUMENTS

| | | | |
|---|---|---|---|
| 5,160,341 A | 11/1992 | Brenneman et al. | |
| 5,304,121 A | 4/1994 | Sahatjian | |
| 5,397,355 A | 3/1995 | Marin et al. | |
| 5,443,477 A | 8/1995 | Marin et al. | |
| 5,571,135 A | 11/1996 | Fraser et al. | |
| 5,601,568 A | 2/1997 | Chevillon et al. | |
| 5,618,300 A | 4/1997 | Marin et al. | |
| 5,707,376 A | 1/1998 | Kavteladze et al. | |
| 5,725,572 A | 3/1998 | Lam et al. | |
| 5,741,270 A | 4/1998 | Hansen et al. | |
| 5,817,152 A | 10/1998 | Birdsall et al. | |
| 5,833,694 A | 11/1998 | Poncet | |
| 5,944,727 A | 8/1999 | Ahari et al. | |
| 5,968,052 A | 10/1999 | Sullivan, III et al. | |
| 5,968,088 A | 10/1999 | Hansen et al. | |
| 6,007,543 A | 12/1999 | Ellis et al. | |
| 6,036,725 A | 3/2000 | Avellanet | |
| 6,110,198 A | 8/2000 | Fogarty et al. | |
| 6,123,722 A | 9/2000 | Fogarty et al. | |
| 6,126,685 A | 10/2000 | Lenker et al. | |
| 6,146,358 A | 11/2000 | Rowe | |
| 6,238,402 B1 | 5/2001 | Sullivan et al. | |
| 6,338,739 B1 | 1/2002 | Datta et al. | |
| 6,391,050 B1 | 5/2002 | Broome | |
| 6,402,760 B1 | 6/2002 | Fedida | |
| 6,428,566 B1 | 8/2002 | Holt | |
| 6,514,261 B1 | 2/2003 | Randall et al. | |
| 6,517,573 B1 | 2/2003 | Pollock et al. | |
| 6,520,934 B1 | 2/2003 | Lee et al. | |
| 6,520,983 B1 | 2/2003 | Colgan et al. | |
| 6,599,296 B1 | 7/2003 | Gillick et al. | |
| 6,660,031 B2 | 12/2003 | Tran et al. | |
| 6,755,854 B2 | 6/2004 | Gillick et al. | |
| 7,001,422 B2 | 2/2006 | Escamilla et al. | |
| 7,052,511 B2 | 5/2006 | Weldon | |
| 7,105,016 B2 | 9/2006 | Shiu et al. | |
| 7,166,125 B1 | 1/2007 | Baker et al. | |
| 7,172,617 B2 | 2/2007 | Colgan et al. | |
| 7,300,456 B2 | 11/2007 | Andreas et al. | |
| 7,320,702 B2 | 1/2008 | Hammersmark et al. | |
| 7,323,006 B2 | 1/2008 | Andreas et al. | |
| 7,326,203 B2 | 2/2008 | Papineau et al. | |
| 7,331,992 B2 | 2/2008 | Randall et al. | |
| 7,351,255 B2 | 4/2008 | Andreas | |
| 7,402,168 B2 | 7/2008 | Sanderson et al. | |
| 7,611,497 B2 | 11/2009 | Wollschlager | |
| 7,674,282 B2 | 3/2010 | Wu et al. | |
| 7,763,063 B2 | 7/2010 | Arbefeuille et al. | |
| 7,799,065 B2 | 9/2010 | Pappas | |
| 7,896,911 B2 | 3/2011 | Schneider et al. | |
| 7,905,913 B2 | 3/2011 | Chew et al. | |
| 7,918,880 B2 | 4/2011 | Austin | |
| 7,963,987 B2 | 6/2011 | Melsheimer et al. | |
| 8,075,607 B2 | 12/2011 | Melsheimer et al. | |
| 8,092,468 B2 | 1/2012 | Hansen | |
| 8,100,958 B2 | 1/2012 | Fischer et al. | |
| 8,128,677 B2 | 3/2012 | Schneider et al. | |
| 8,366,766 B2 | 2/2013 | Berreklouw | |
| 8,414,636 B2 | 4/2013 | Nabulsi et al. | |
| 8,500,789 B2 | 8/2013 | Wuebbeling et al. | |
| 8,585,747 B2 | 11/2013 | Andreas et al. | |
| 2002/0055772 A1 | 5/2002 | McGuckin, Jr. et al. | |
| 2002/0099435 A1* | 7/2002 | Stinson | A61F 2/90 623/1.12 |
| 2002/0123790 A1 | 9/2002 | White et al. | |
| 2002/0143386 A1* | 10/2002 | Davila | A61F 2/91 623/1.15 |
| 2002/0151955 A1 | 10/2002 | Tran et al. | |
| 2002/0156496 A1 | 10/2002 | Chermoni | |
| 2003/0018377 A1 | 1/2003 | Berg et al. | |
| 2003/0069630 A1* | 4/2003 | Burgermeister | A61F 2/91 623/1.15 |
| 2003/0225446 A1 | 12/2003 | Hartley | |
| 2004/0158308 A1 | 8/2004 | Hogendijk et al. | |
| 2004/0186551 A1 | 9/2004 | Kao et al. | |
| 2005/0060016 A1 | 3/2005 | Wu et al. | |
| 2005/0107865 A1* | 5/2005 | Clifford | A61F 2/91 623/1.16 |
| 2005/0171592 A1 | 8/2005 | Majercak | |
| 2005/0246008 A1 | 11/2005 | Hogendijk et al. | |
| 2005/0288764 A1 | 12/2005 | Snow et al. | |
| 2005/0288766 A1 | 12/2005 | Plain et al. | |
| 2006/0111769 A1 | 5/2006 | Murray | |
| 2006/0184225 A1 | 8/2006 | Pryor | |
| 2006/0193892 A1 | 8/2006 | Furst et al. | |
| 2006/0206190 A1 | 9/2006 | Chermoni | |
| 2006/0229700 A1 | 10/2006 | Acosta et al. | |
| 2006/0271151 A1 | 11/2006 | McGarry et al. | |
| 2006/0276871 A1 | 12/2006 | Lamson et al. | |
| 2006/0282147 A1* | 12/2006 | Andreas | A61F 2/91 623/1.11 |
| 2006/0282149 A1 | 12/2006 | Kao | |
| 2007/0088420 A1 | 4/2007 | Andreas et al. | |
| 2007/0118201 A1 | 5/2007 | Pappas et al. | |
| 2007/0142892 A1* | 6/2007 | Dave | A61F 2/95 623/1.11 |
| 2007/0156223 A1 | 7/2007 | Vaughan | |
| 2007/0156225 A1 | 7/2007 | George et al. | |
| 2007/0179587 A1 | 8/2007 | Acosta et al. | |
| 2007/0276461 A1 | 11/2007 | Andreas et al. | |
| 2008/0033522 A1 | 2/2008 | Grewe et al. | |
| 2008/0051867 A1 | 2/2008 | Davila et al. | |
| 2008/0082154 A1 | 4/2008 | Tseng et al. | |
| 2008/0132989 A1* | 6/2008 | Snow | A61F 2/95 623/1.12 |
| 2008/0255653 A1 | 10/2008 | Schkolnik | |
| 2008/0264102 A1 | 10/2008 | Berra | |
| 2008/0319528 A1 | 12/2008 | Yribarren et al. | |
| 2009/0018637 A1 | 1/2009 | Paul, Jr. et al. | |
| 2009/0024133 A1 | 1/2009 | Keady et al. | |
| 2009/0270967 A1 | 10/2009 | Fleming III et al. | |
| 2009/0276031 A1 | 11/2009 | Kao | |
| 2010/0137966 A1* | 6/2010 | Magnuson | A61F 2/95 623/1.11 |
| 2010/0234932 A1* | 9/2010 | Arbefeuille | A61F 2/95 623/1.11 |
| 2010/0318173 A1 | 12/2010 | Kolandaivelu et al. | |
| 2011/0004237 A1 | 1/2011 | Schneider et al. | |
| 2011/0071621 A1 | 3/2011 | Griego et al. | |
| 2011/0077731 A1 | 3/2011 | Lee et al. | |
| 2011/0152992 A1 | 6/2011 | Schneider et al. | |
| 2011/0301685 A1 | 12/2011 | Kao | |
| 2011/0301690 A1 | 12/2011 | Giasolli et al. | |
| 2011/0307049 A1 | 12/2011 | Kao | |
| 2012/0035705 A1 | 2/2012 | Giasolli et al. | |
| 2012/0083872 A1 | 4/2012 | Schneider et al. | |
| 2012/0172963 A1 | 7/2012 | Ryan et al. | |
| 2013/0144375 A1* | 6/2013 | Giasolli | A61F 2/82 623/1.16 |

FOREIGN PATENT DOCUMENTS

| | | |
|---|---|---|
| WO | WO 96/09013 | 3/1996 |
| WO | WO 01/76509 | 10/2001 |
| WO | WO 03/047651 | 6/2003 |
| WO | WO 2004/032799 | 4/2004 |
| WO | WO 2007/109621 | 9/2007 |

\* cited by examiner

FIG. 6E

DELIVERY DEVICE AND METHOD OF DELIVERY

INCORPORATION BY REFERENCE TO ANY PRIORITY APPLICATIONS

This application is a continuation of U.S. patent application Ser. No. 14/656,462, filed Mar. 12, 2015, which claims the benefit of priority of U.S. Provisional Appl. No. 62/109,534, filed Jan. 29, 2015. All of the above applications are incorporated by reference herein and are to be considered a part of this specification. Any and all applications for which a foreign or domestic priority claim is identified in the Application Data Sheet as filed with the present application are hereby incorporated by reference under 37 CFR 1.57.

BACKGROUND OF THE INVENTION

1. Field of the Invention

Disclosed herein are delivery devices and methods of delivery. Certain embodiments are described with reference to sequential delivery of multiple intraluminal devices from a delivery device. The delivery devices and methods can be used in procedures to treat atherosclerotic occlusive disease, though they are not limited to these procedures.

2. Description of the Related Art

There are a number of medical conditions and procedures in which a device such as a stent is placed in the body to create or maintain a passage. There are a wide variety of stents used for different purposes, from expandable coronary, vascular and biliary stents, to plastic stents used to allow the flow of urine between kidney and bladder.

Stents are often placed in the vascular system after a medical procedure, such as balloon angioplasty. Balloon angioplasty is often used to treat atherosclerotic occlusive disease. Atherosclerotic occlusive disease is the primary cause of stroke, heart attack, limb loss, and death in the US and the industrialized world. Atherosclerotic plaque forms a hard layer along the wall of an artery and can be comprised of calcium, cholesterol, compacted thrombus and cellular debris. As the atherosclerotic disease progresses, the blood supply intended to pass through a specific blood vessel is diminished or even prevented by the occlusive process. One of the most widely utilized methods of treating clinically significant atherosclerotic plaque is balloon angioplasty, which may be followed with stent placement.

SUMMARY OF THE INVENTION

Currently available stents and stent delivery systems have many limitations and drawbacks. There exists a continuing need for improvement in intraluminal devices and associated delivery devices.

According to certain embodiments, a delivery device can be provided for sequential delivery of a plurality of intraluminal devices (e.g. stents, tacks, staples, etc.) held in a compressed state on the delivery device. For purposes of this disclosure the word tack will be used to describe one of many intraluminal devices which can be deployed from a delivery device. The delivery device can comprise a plurality of delivery platforms, each delivery platform configured for holding a tack in a compressed position on the delivery device and having a unique shape, such as a non-constant outer diameter, an hourglass shape, a tapered proximal half, ridges, dimples, etc. This unique shape can be positioned between annular pusher bands that may also be radiopaque markers.

In some embodiments, the unique shape is provided by a sleeve of flexible material with the unique shape surrounding a harder inner shaft. Further, the annular pusher bands can be made of wire or sections of material to increase flexibility while remaining radiopacity.

A tack deployment method can include alignment of radiopaque markers on the outer sheath and the tack to be deployed prior to deployment.

A method of marker band alignment and intraluminal device or tack delivery can be performed. The method can include: advancing a delivery device with a plurality of tacks in a compressed state to a treatment area; each tack comprising a plurality of struts and a radiopaque marker positioned in a central region of the tack, each tack being a same size with the radiopaque marker positioned in a same location; the delivery device comprising an inner core having a plurality of delivery platforms, each delivery platform having one of the plurality of tacks, and an outer sheath covering the inner core and the delivery platforms, the outer sheath having a radiopaque marker band positioned proximally from a distal end; withdrawing the outer sheath until the radiopaque marker band on the outer sheath and radiopaque marker on a first tack to be delivered are aligned; aligning these two radiopaque markers with a treatment area such as a tissue dissection or lesion to be treated before release of the tack; then withdrawing the outer sheath to release the tack.

In some embodiments, a delivery device can comprise an inner shaft, a delivery platform and an outer sheath. The delivery platform can include a pair of annular bands around the inner shaft, both of the annular bands having a first outer diameter and a sleeve. The sleeve can be secured to the inner shaft and positioned between the annular bands. The sleeve can have a lower durometer than the inner shaft and optimally also lower than the pair of annular bands. The sleeve can further have a non-constant outer diameter being less than the first outer diameter of the annular bands. The delivery platform can be configured to receive an intraluminal device for deployment from the delivery device into a vessel and to receive the intraluminal device between the annular bands and on the sleeve. The outer sheath can be positioned on and slidable over the inner shaft and the delivery platform, the outer sheath having a pre-deployment position covering the delivery platform and at least one delivery position where the outer sheath is withdrawn exposing at least one of the annular bands and the sleeve of the delivery platform.

According to some embodiments, a plurality of additional delivery platforms can be included for sequential delivery of a plurality of intraluminal devices. Each additional delivery platform can comprise an additional sleeve and an additional annular band. Each of the annular bands can have a radius on a proximal end and/or comprise a radiopaque helical coil. The radiopaque helical coil can be encased in a polymer having a higher durometer than a polymer that forms the sleeve.

The sleeve can include any number of different shapes and sizes, and can include ridges, dots, dimples, etc.

In some embodiments, a delivery device can comprise an inner shaft, the inner shaft having a nose cone on the distal tip; a delivery platform; and an outer sheath. The delivery platform can comprise a pair of annular bands secured to the inner shaft, both of the annular bands having a first outer diameter; and a sleeve secured to the inner shaft and positioned between the annular bands. The sleeve can have a lower durometer than the inner shaft and optionally also the pair of annular bands. The sleeve may further have a first constant outer diameter section and a second constant outer diameter section having a larger outer diameter than the first, but less than the first outer diameter of the annular bands, and the second constant outer diameter section having a shorter axial length than the first constant outer diameter section, the sleeve further having a smooth tapered transition between the first and second constant outer diameter sections. The delivery platform can be configured to receive an intraluminal device for deployment from the delivery device into a vessel and configured to receive the intraluminal device between the annular bands and on the sleeve. The outer sheath can be positioned on and slidable over the inner shaft and the delivery platform. The outer sheath can have a pre-deployment position covering the delivery platform and at least one delivery position where the outer sheath is withdrawn exposing at least one of the annular bands and the sleeve of the delivery platform.

An intraluminal device deployment method can include one or more of the following steps. Advancing a delivery device with a plurality of intraluminal devices in a compressed state to a treatment area. Each of the plurality of intraluminal devices can comprise a plurality of struts and a radiopaque marker positioned in a central region of the intraluminal device. Each of the plurality of intraluminal devices can be a same size with the radiopaque marker positioned in a same location. The delivery device can comprise an inner shaft having a plurality of delivery platforms, each intraluminal device of the plurality of intraluminal devices positioned at a respective delivery platform of the plurality of delivery platforms, and an outer sheath covering the inner shaft and the plurality of delivery platforms, the outer sheath having a radiopaque marker band positioned proximally from a distal end of the outer sheath. Withdrawing the outer sheath until the radiopaque marker band on the outer sheath and radiopaque marker on a first intraluminal device to be delivered of the plurality of intraluminal devices are aligned. Aligning the aligned radiopaque marker band and the radiopaque marker with the treatment area before release of the first intraluminal device. Withdrawing the outer sheath to release the first intraluminal device. Withdrawing the outer sheath until the radiopaque marker band on the outer sheath and radiopaque marker on a second intraluminal device to be delivered of the plurality of intraluminal devices are aligned.

In some embodiments of the method, aligning the aligned radiopaque marker band and the radiopaque marker with the treatment area can comprise centering the aligned radiopaque marker band and the radiopaque marker at a tissue dissection before release of the first intraluminal device. In some embodiments of the method, withdrawing the outer sheath until the radiopaque marker band on the outer sheath and radiopaque marker on the first intraluminal device to be delivered of the plurality of intraluminal devices are aligned can comprise withdrawing the outer sheath until a distal-most end of the outer sheath and a distal-most end of the first intraluminal device are aligned. In some embodiments of the method, withdrawing the outer sheath until the radiopaque marker band on the outer sheath and radiopaque marker on the first intraluminal device to be delivered of the plurality of intraluminal devices are aligned can comprise withdrawing the outer sheath until the radiopaque marker band is positioned at a middle of the first intraluminal device. In some embodiments of the method, the first intraluminal device can have a single column of radiopaque markers and withdrawing the outer sheath until the radiopaque marker band on the outer sheath and radiopaque marker on the first intraluminal device to be delivered of the plurality of intraluminal devices are aligned can comprise withdrawing the outer sheath until the radiopaque marker band encircles the single column of radiopaque markers.

BRIEF DESCRIPTION OF THE DRAWINGS

Various embodiments are depicted in the accompanying drawings for illustrative purposes, and should in no way be interpreted as limiting the scope of the inventions, in which like reference characters denote corresponding features consistently throughout similar embodiments.

DETAILED DESCRIPTION OF THE PREFERRED EMBODIMENT

A delivery device 10 can be used as part of a procedure to treat atherosclerotic occlusive disease. The delivery device can be used to deliver one or more intraluminal devices 2, such as tacks, to a site of plaque accumulation. The tacks can stabilize the site and/or hold pieces of plaque out of the way of blood flow. It will be understood that though the delivery devices and methods described herein are described primarily with reference to vascular procedures, they can also be used in treatments for other parts of the body.

Figure 1:
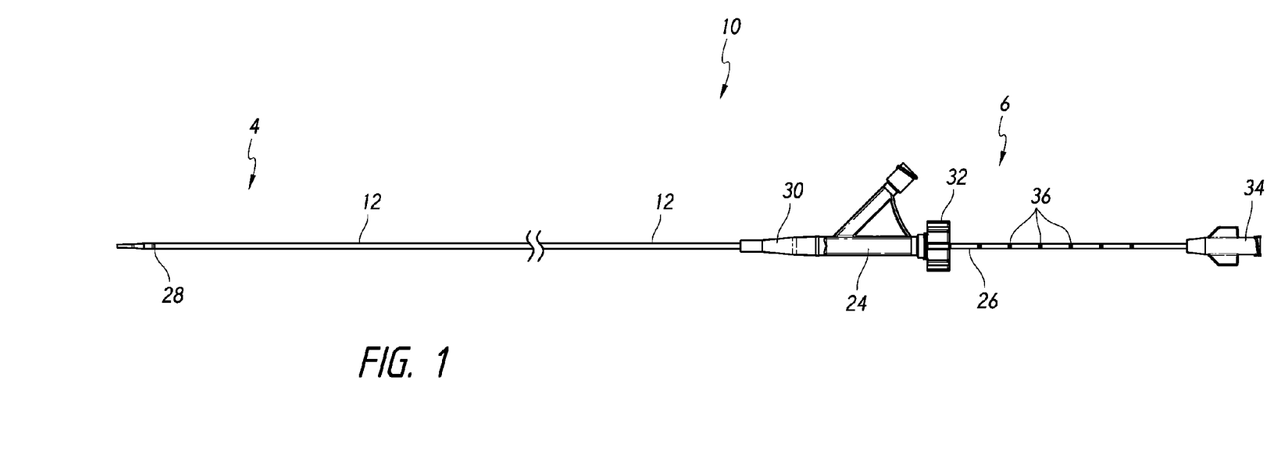
FIG. 1 is a side view of a delivery device that has been shortened to facilitate illustration.
Figure 2:
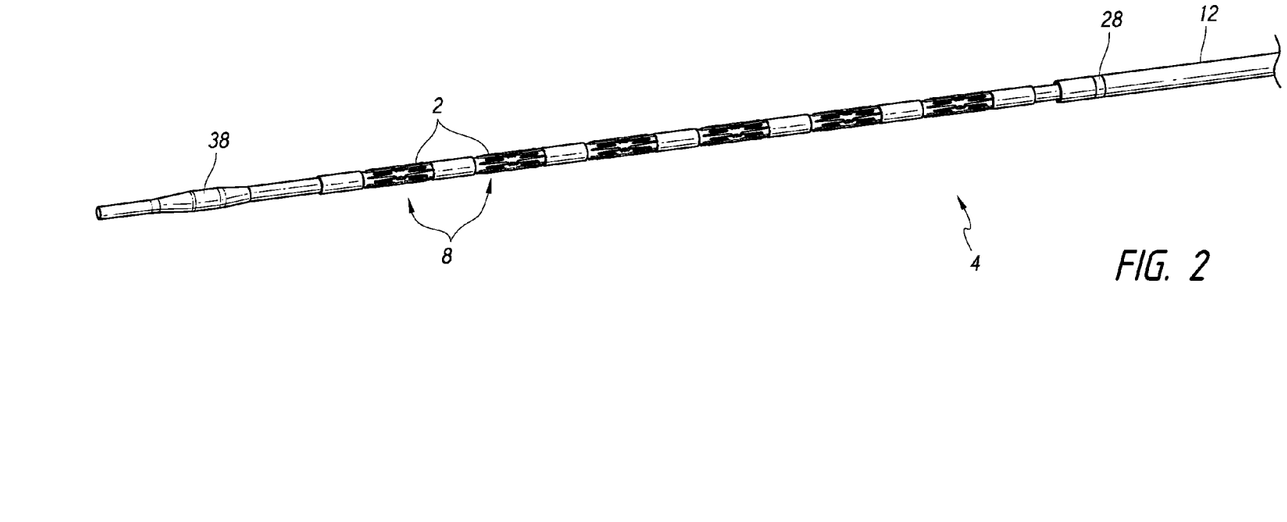
FIG. 2 shows a view of the distal end of the delivery device with an outer sheath withdrawn.

FIGS. 1 and 2 illustrate an embodiment of delivery device 10 that can be used for sequential delivery of multiple intraluminal devices 2. The delivery device 10 can be used in procedures to treat atherosclerotic occlusive disease, though it is not limited to these procedures.

The delivery device 10 of FIG. 1, which has been shortened to facilitate illustration, highlights the distal 4 and proximal ends 6. The proximal end 6 can be held by a physician or other medical professional during a medical procedure. It is used to control delivery of one or more intraluminal devices or tacks 2. FIG. 2 shows the distal end 4 with six (6) intraluminal devices 2, each positioned at a dedicated delivery platform 8. Comparing FIGS. 1 and 2, it can be seen that an outer sheath 12 has been withdrawn from the distal end in FIG. 2. This reveals the delivery platforms 8 and the respective intraluminal devices 2. The intraluminal devices 2 are preferably self-expandable and are shown in their compressed position to represent how they would fit in the delivery platforms. In typical use, the outer sheath 12 would be covering the intraluminal devices 2 when in this position. As will be discussed in more detail below, the outer sheath 12 can be withdrawn in a systematic manner to deploy one intraluminal device 2 at a time at a desired treatment location.

Figures 3, 3A:
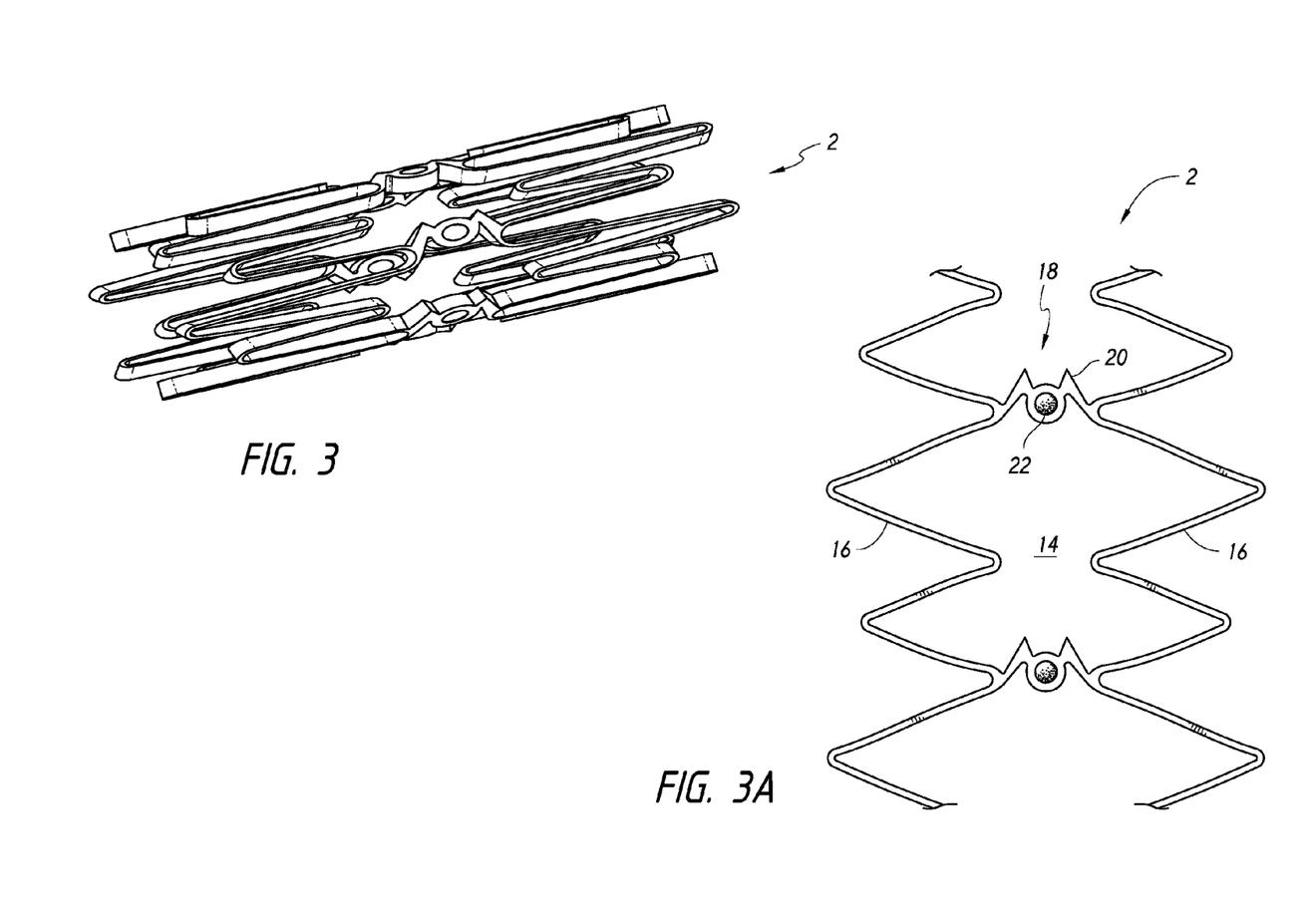
FIG. 3 shows an embodiment of intraluminal device or tack.
FIG. 3A shows a flattened section of the tack of FIG. 3.

Relatively small intraluminal devices 2, for example with only one (FIGS. 3 & 3A) or two columns of cells, can be delivered at precise treatment locations and space appropriately to not overlap. FIG. 3A shows a flattened section of the tack of FIG. 3. It can be seen that a single column of cells 14 are formed by two concentric rings of undulating struts 16 connected by bridge members 18. The bridge members 18 have a pair of anchors 20 and a radiopaque marker 22. Multiple small intraluminal devices 2 can be used to treat a single or multiple lesions. This can minimize the amount of foreign material in the body, while providing needed holding forces. Various embodiments of intraluminal devices and delivery devices are described in more detail in Applicants' related patent application Ser. No. 13/179,458 filed Jul. 8, 2011, published as US 2012/0035705 (IVAS.002P4) and patent application Ser. No. 13/749,643 filed Jan. 24, 2013, published as US 2013/0144375 (IVAS.002P6), both of which are incorporated by reference herein and made a part of this specification.

It will be understood, that the delivery devices and methods can also be used for other intraluminal devices 2, including larger devices, and are not limited to use with intraluminal devices 2 having only one or two columns of cells.

Returning now to FIG. 1, the proximal end 6 of the illustrated embodiment will now be described. The delivery device 10 can include an outer sheath 12, a proximal housing 24, and an inner shaft 26. The outer sheath 12 can be constructed as a laminate of polymer extrusions and braided wires embedded in the polymer extrusions. Flexibility and stiffness can be controlled through the number of braid wires, the braid pattern and pitch of the braid. In other embodiments, the outer sheath can be formed of a hypotube, such as a metal or plastic hypotube. Flexibility and stiffness of the sheath can be controlled by many features such as the slope and frequency of a spiral cut along the length of the hypotube. The outer sheath may also include a radiopaque (RO) marker 28 at or near the distal end. In some embodiments, the radiopaque marker 28 can be an annular band spaced from the distal-most end.

As shown, the outer sheath 12 is a braided shaft and the proximal housing 24 is a bifurcation luer that connects to the outer sheath through a strain relief 30. The strain relief 30 can take any form, such as being made of polyolefin or other similar material.

The bifurcation luer 24 has a main arm to receive the inner shaft 26 and a side arm. The bifurcation luer can be disposed at the proximal end of the outer sheath. The side arm includes a flushing port that is used to flush out air and increase lubricity in the space between the sheath and the inner shaft.

A tuohy borst adapter, hemostatic valve, or other sealing arrangement 32 can be provided proximal of or integrated into the bifurcation luer 24 to receive and seal the proximal end of the space between the inner shaft 26 and the outer sheath 12. The tuohy borst adapter can also provide a locking interface, such as a screw lock, to secure the relationship between the outer sheath and the inner shaft. This can allow the physician to properly place the distal end without prematurely deploying a tack.

The inner shaft is shown with a proximal luer hub 34 and deployment reference marks 36. The deployment reference marks 36 can correspond with the delivery platforms 8, such that the spacing between each deployment reference mark can be the same as the spacing between features of the delivery platforms. For example, the space between deployment reference marks can be the same as the distance between the centers of the delivery platforms.

In some embodiments, a distal most deployment reference mark, or a mark that is different from the others, such as having a wider band or different color, can indicate a primary or home position. For example a deployment reference mark with a wider band than the others can be aligned with the proximal end of the bifurcation luer 24 or hemostatic valve 32. This can indicate to a physician that the outer sheath is in a position completely covering the inner shaft 26 proximal of the nose cone 38. In some embodiments, this alignment can also translate to alignment of the RO marker 28 on the outer sheath to a RO marker on the distal end of the inner shaft 26.

In some embodiments, one or more of the deployment reference marks 36 can represent the number of tacks that are within the system. Thus, once a tack is released, the deployment reference mark 36 will be covered up and the physician can know that the remaining deployment reference marks correspond with the remaining number of tacks available for use. In such an embodiment, the proximal end of the bifurcation luer 24 or hemostatic valve 32 can be advanced to be centered approximately between two reference marks to indicate deployment.

Figure 4:
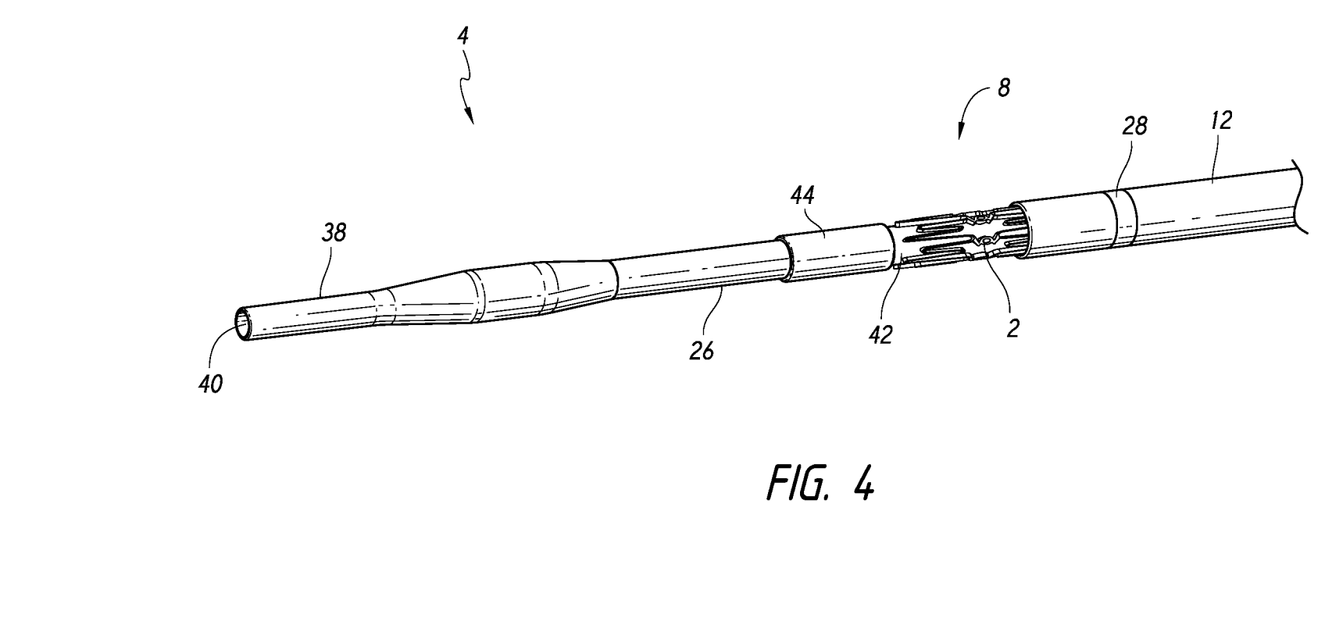
FIG. 4 illustrates a detail view of the distal end of the delivery device with the outer sheath partially withdrawn.

Looking now to FIG. 4, a detail view of the distal end 4 of the delivery device 10 is shown. Features of the illustrated embodiment include the inner shaft 26 with a distal soft tip 38. The tip 38 can be a tapered nose cone. The nose cone 38 serve as a dilating structure to atraumatically displace tissue and help to guide the delivery device through the vasculature. The tip 38 itself may be radiopaque, or a radiopaque element 27 can be incorporated into or near the tip. A guidewire lumen 40 can be seen that extends through the inner shaft 26 to the proximal luer hub 34 (FIG. 1). The guidewire lumen 40 is configured for receipt and advancement of a guidewire therein.

Parts of a delivery platform 8 are also shown. The delivery platforms 8 are identical in the illustrated embodiment, though other embodiments can have different sizes and constructions between different delivery platforms. A crimped or compressed tack 2 is shown in the delivery platform 8.

Figure 5:
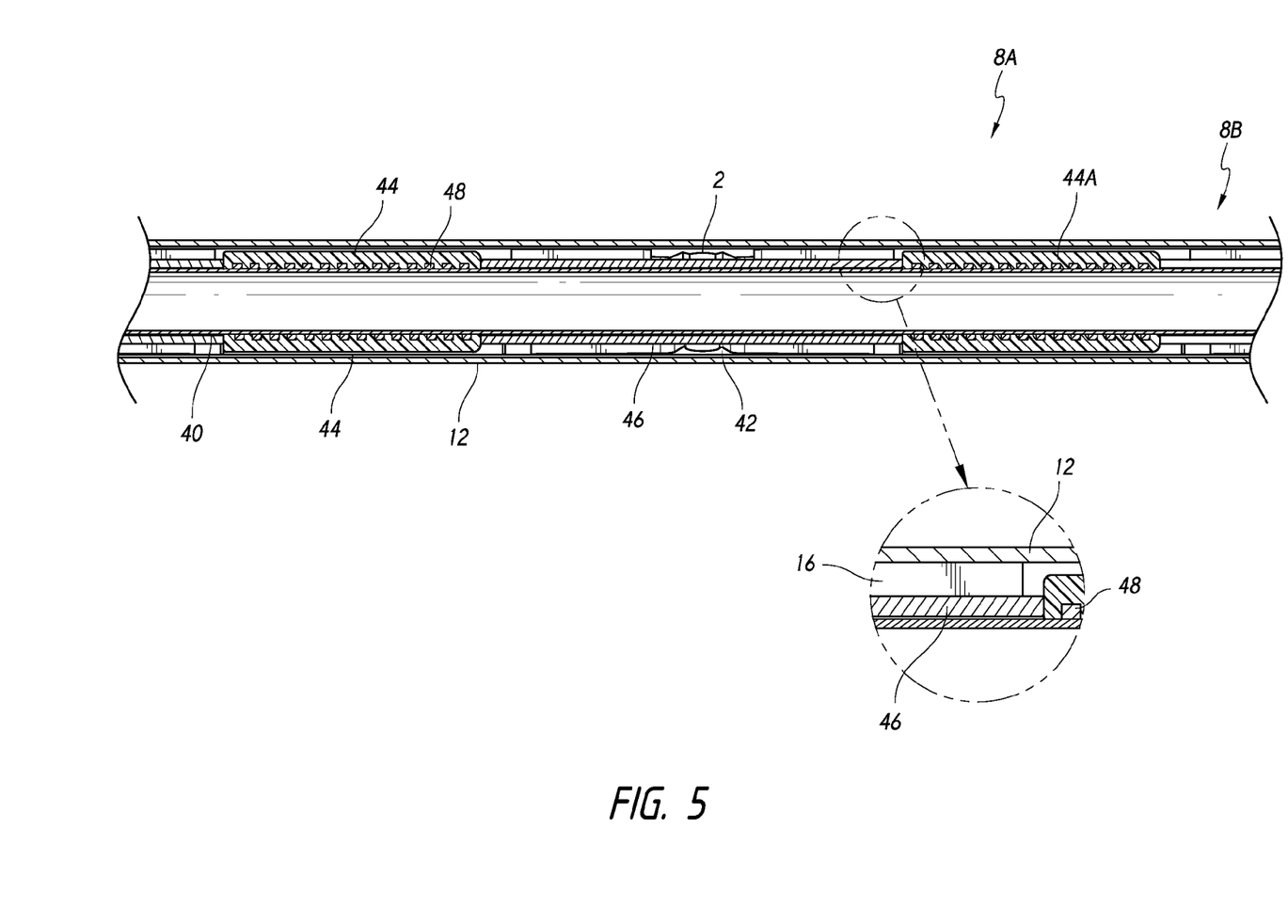
FIG. 5 is a cross section of a delivery device showing an embodiment of delivery platform.

As can be seen in FIGS. 2 and 4, one or more delivery platforms 8 can be disposed on the inner shaft 26 adjacent the distal end 4 of the delivery device 10. Each of the delivery platforms 8 can comprise a recess 42 extending positioned between a pair of annular pusher bands 44. FIG. 5 shows a cross section of a delivery device at one embodiment of delivery platform 8A. In the illustrated embodiment, the proximal annular pusher band 44A of a first platform 8A is also the distal annular pusher band 44A of the platform 8B located immediately proximal (only partially shown). The annular pusher band 44 has a larger outer diameter as compared to the delivery platform at the recess 42. In some embodiments, the recess can be defined as the smaller diameter region next to, or between, one or two annular pusher bands and/or an additional feature on the inner shaft 26.

One or more of the annular pusher bands 44 can be radiopaque marker bands. For example, proximal and distal radiopaque marker bands 44 can be provided to make the ends of the platform 8 visible using standard visualization techniques. The annular marker bands 44 can take any suitable form, for example including one more of tantalum, iridium, and platinum materials. In some embodiments, the pusher bands 44 can be 4 mm long with 6.75 mm recesses between them. A tack of 6.5 mm can be positioned between the pusher bands 44. In some embodiments, the pusher bands can be between 50-70% of the size of the recess and/or the tack. In some embodiments, the pusher bands are about 60%. In other embodiments, the pusher bands can be much smaller, at between 10-20% of the size of the recess and/or the tack. This may be the case especially with longer tacks. In some embodiments, at least the proximal ends of the pusher bands 44 can have a radius to help reduce potential for catching on deployed tacks during retraction of the delivery device.

Reducing the difference in length between the recess and the tack can increase the precision of placement of the tack, especially with tacks having only one or two columns of cells. In some embodiments, the recess can be less than 1, 0.5, 0.4, 0.3, 0.25, or 0.2 mm longer than the tack. The tack can be any number of different sizes, such as 4, 5, 6, 6.5, 8, 10, or 12 mm in length.

The outer sheath 12 can be made of polyether block amide (PEBA), a thermoplastic elastomer (TPE) available under the trade name PEBAX. In some embodiments, the outer sheath 12 can have a thinner inner liner made of a polytetrafluoroethylene (PTFE) such as TEFLON. Any radiopaque marker band(s) 28 or other radiopaque material may be positioned between these two layers. In other embodiments, the radiopaque marker band(s) 28, or other radiopaque material can be embedded within one or more layers of the outer sheath 12. The radiopaque marker band(s) 28 can range from 0.5 mm to 5 mm wide and be located from 0.5 mm to 10 mm proximal from the distal-most tip 52. In some embodiments, the radiopaque marker band(s) 28 can be 1 mm wide and 3 mm proximal from the distal-most tip 52.

In the cross section of FIG. 5 it can be seen that a sleeve 46 is positioned around the inner shaft 26 between the two annular bands 44. In some embodiments, a delivery platform 8 can comprise a sleeve 46 surrounding a shaft 26, where the sleeve 46 is made of a different material, or has different material properties, than the shaft 26. In some embodiments, the sleeve provides a material having a tackiness, a grip, a tread pattern, and/or other features to help the tack stay in place in the delivery platform. In some embodiments, the sleeve can be made of PEBA. The inner shaft according to some embodiments is a composite extrusion made of a PTFE/polyimide composite. The sleeve can be softer than (a lower durometer than) the inner shaft and/or the pusher bands 44. This may be the case even if made of similar types of materials. In some embodiments, the sleeve can be a material having a tackiness, a grip, a tread pattern, and/or other features to help the tack stay in place (e.g. longitudinal position with respect to the inner shaft) while the outer sleeve 12 is withdrawn. This can increase the amount of control during deployment and reduce the likelihood that the tack will shoot out distally from the delivery platform (known in the industry as watermelon seeding). In some cases the outer sheath can be partially removed thereby partially exposing an intraluminal device whereby the intraluminal device can partially expand while being securely retained by the delivery prior to full release.

The sleeve 46 can be sized so that with the tack 2 in the delivery platform 8 there is minimal to no space between the tack and the outer sheath. In some embodiments, the sleeve 46 can be co-molded with or extruded onto the inner shaft 26. In some embodiments, the delivery device 10 can be formed with a single sleeve 46 extending over a length of the inner shaft 26. For example, the sleeve can extend from the first delivery platform to the last delivery platform. The annular bands 44 may surround distinct sections of sleeve 46, or they may be encased by the sleeve 46. In some embodiments, each delivery platform 8 has a separate sleeve 46 positioned in the recess 42. The annular bands 44 may be encased by a different material, or may not be encased at all.

Figures 6A, 6B, 6C, 6D:
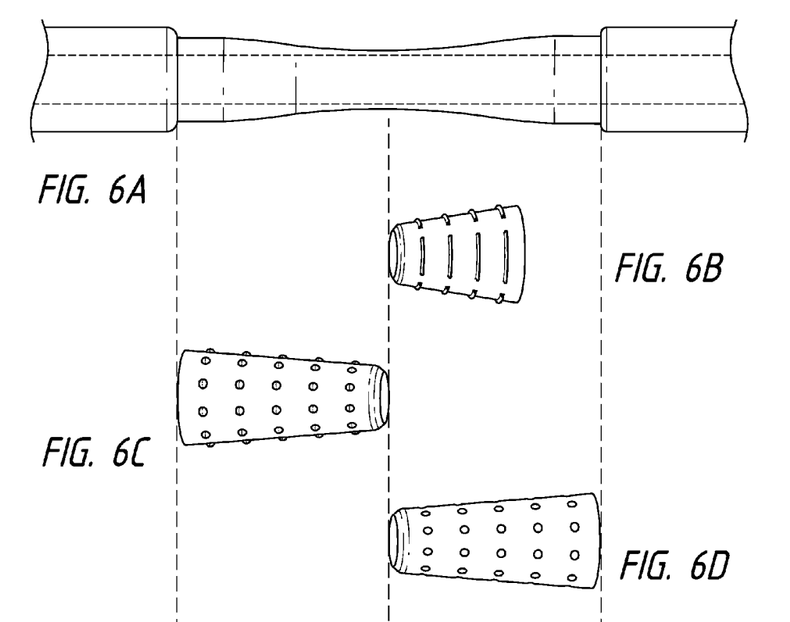
FIGS. 6A-E illustrate various embodiments of delivery platforms having different shapes.

As will be understood from FIG. 5, the sleeve 46 can be cylindrical with a circular cross-section that is maintained across a portion of or the entire length of sleeve. In other embodiments, the sleeve has a unique shape and may include one or more of the following: tapering (FIGS. 6A-E), an hourglass shape (FIG. 6A), ridges (FIG. 6B), dimples (FIG. 6C), dots (FIG. 6D), two or more different diameters (FIG. 6E), etc. Features such as ridges, dots, and dimples can be positioned in number of different patterns or groupings. In addition, the sleeve (FIGS. 6B-D), or a section of the sleeve (FIG. 6E) can extend along less than the entire recess. In some embodiments, the length of the sleeve or larger outer diameter section can correspond to the length of the tack. For example, the sleeve or larger diameter section can extend ¾, ⅔, ½, ⅖, ⅓, ¼ of the recess and/or tack. Further, the length of the sleeve or larger outer diameter section can be related to the size of struts in the undulating ring 16, such as a proximal most undulating ring. For example, it can extend along the entire, ⅘, ¾, ⅔, or ½ of the length of a strut or the length of the proximal most undulating ring. A short sleeve, or a larger outer diameter section of a sleeve, preferably extends from the proximal end of the recess distally (FIGS. 6D-E), but can also be centered in the recess, positioned on at the distal end (FIG. 6C), or at other positions within the recess.

Figure 6E:
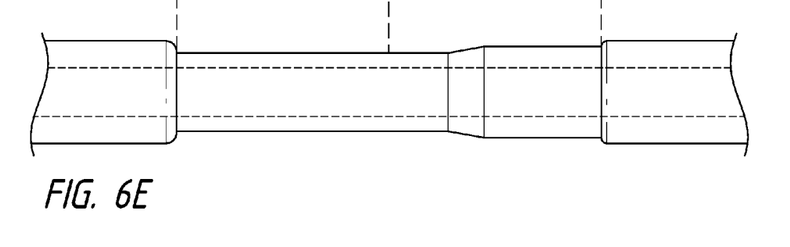

The sleeve of FIG. 6E is shown having two different constant outer diameter sections with a short taper between them. The sleeve can be formed from two separate sections that are thermally bonded together. The tapered portion can also be created by thermal bonding so that there is a smooth transition between the two constant outer diameter sections. As has been mentioned, the larger constant outer diameter section preferably extends from the proximal end of the recess distally. This larger outer diameter section that may or may not have a constant outer diameter can extend along less than the entire recess as has been discussed above.

In some embodiments, an inner shaft 26 can have a lower durometer sleeve 46 between pushers 44. A tack 2 can be crimped onto the sleeve 46 and an outer sheath 12 can constrain the crimped tack in place. The clearance between the sleeve 46 and the outer sheath 12 can result in a slight interference fit between the crimped tack 2 and the inner and outer elements. This slight interference allows the delivery system to constrain the crimped tack during deployment until it is almost completely unsheathed allowing the distal portion of the tack to "flower petal" open and engage the vessel wall, reducing the potential for jumping.

According to some embodiments, the inner shaft 26 can be made of a polyimide-PEBA combination and the lower durometer PEBA sleeve 46 can be thermally bonded in between pushers 44. A tack 2 can be crimped onto the sleeve 46 and a PTFE lined outer sheath 12 can constrain the crimped tack in place.

Returning to FIG. 5, a feature of certain embodiments of radiopaque marker band 44 is shown. As has been mentioned, the sleeve 46 may encase the annular bands 44. Alternatively, another material can encase the metallic bands to form the annular marker bands 44. The annular marker bands 44 can be made of wire 48 or multiple pieces of material or having slits to increase flexibility while remaining radiopacity. In some embodiments the wire can form a helical coil that is wrapped around the inner shaft 26.

Moving now to FIGS. 7A-C, certain methods of deployment will now be described. A delivery device 10 can be used as part of a procedure to treat atherosclerotic occlusive disease. The delivery device can be used to deliver one or more intraluminal devices 2, such as tacks, to a site of plaque accumulation. The tacks can stabilize the site and/or hold pieces of plaque out of the way of blood flow.

The tacks are preferably self-expandable. Thus, withdrawing the sheath 12 to reveal a tack 2 allows the tack to deploy from the delivery device 10 by self-expansion. The sheath can be withdrawn in small increments to sequentially deliver tacks at desired locations in a blood vessel. In some embodiments, the small increments can correspond with the deployment reference marks 36. The deployment reference marks 36 can be spaced apart at least the length of the tack, so that each tack can be deployed at once, rather than the gradual release typical of a longer stent. This can allow for more precise placement of the tack.

Balloon angioplasty is an accepted method of opening blocked or narrowed blood vessels in every vascular bed in the body. Balloon angioplasty is performed with a balloon angioplasty catheter. The balloon angioplasty catheter consists of a cigar shaped, cylindrical balloon attached to a catheter. The balloon angioplasty catheter is placed into the artery from a remote access site that is created either percutaneously or through open exposure of the artery. The catheter is passed along the inside of the blood vessel over a wire that guides the way of the catheter. The portion of the catheter with the balloon attached is placed at the location of the atherosclerotic plaque that requires treatment. The balloon is inflated to a size that is consistent with the original diameter of the artery prior to developing occlusive disease. In some instances the balloon is coated with, or otherwise configured to deliver, a drug or biologic to the tissue. When the balloon is inflated, the plaque is broken. Cleavage planes form within the plaque, permitting the plaque to expand in diameter with the expanding balloon. Frequently, a segment of the plaque is more resistant to dilatation than the remainder of the plaque. When this occurs, greater pressure pumped into the balloon results in full dilatation of the balloon to its intended size. The balloon is deflated and removed and the artery segment is reexamined. The process of balloon angioplasty is one of uncontrolled plaque disruption. The lumen of the blood vessel at the site of treatment is usually somewhat larger, but not always and not reliably.

Some of the cleavage planes created by fracture of the plaque with balloon angioplasty can form a dissection. More generally, a dissection occurs when a portion of the plaque or tissue is lifted away from the artery, is not fully adherent to the artery and may be mobile or loose. The plaque or tissue that has been disrupted by dissection protrudes into the flow stream. If the plaque or tissue lifts completely in the direction of blood flow, it may impede flow or cause acute occlusion of the blood vessel. There is evidence that dissection after balloon angioplasty must be treated to prevent occlusion and to resolve residual stenosis. There is also evidence that in some circumstances, it is beneficial to place a metal retaining structure, such as a stent or other intraluminal device to hold open the artery after angioplasty and/or force the dissected material back against the wall of the blood vessel to create an adequate lumen for blood flow.

A variety of delivery methodologies and devices can be used to deploy an intraluminal device, such as a tack 2, some of which are described below. For example, a tack can be delivered into the blood vessel with an endovascular insertion. The delivery devices for the different embodiments of plaque tacks can be different or the same and can have features specifically designed to deliver the specific tack. The tack and installation procedure may be designed in a number of ways that share a common methodology of utilizing an expansion force of the delivery mechanism (such as balloon expansion) and/or the expansion force of an undulating ring to enable the tack to be moved into position in the blood vessel, then released to an expanded state within the blood vessel. A tack deployment method can include alignment of radiopaque markers on the outer sheath and the tack to be deployed prior to deployment.

Figure 7A:
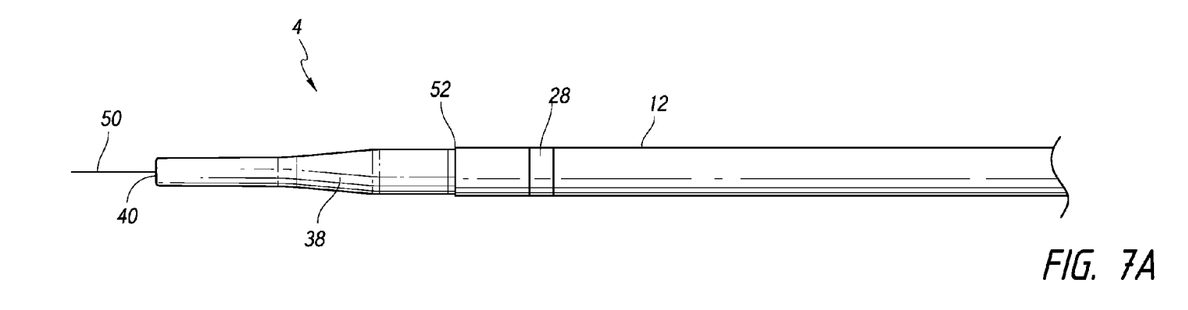
FIGS. 7A-C illustrate certain steps of a deployment method.

Referring now FIG. 7A, a delivery device 10 with an outer sheath 12 is shown in a first pre-deployment state. Multiple tacks 2 can be held by the outer sheath 12 in a compressed state within the delivery device 10. In some embodiments, the tacks 2 are flash frozen in their compressed state to facilitate loading onto the delivery device. The tacks can extend over a given length of the delivery device as has been described.

The delivery device can be advanced over a guidewire 50 in a patient's vasculature to a treatment site. The guidewire 50 can be the same guidewire used in a prior step of a procedure, such as the guidewire used to position an angioplasty balloon. Once positioned at the treatment location, the outer sheath 12 can be withdrawn or retracted to second pre-deployment position (FIG. 7B). The second pre-deployment position can be used to adjust the position of the outer sheath to account for any stretching, tortuosity, etc. that may require some adjustment before releasing a tack. In the second pre-deployment position, the distal end 52 of the outer sheath can be positioned at, or slightly distal of the distal end of a tack to be deployed.

According to some embodiments, the outer sheath 12 can have a radiopaque annular marker band 28 and the tack can also have one or more radiopaque markers 22. The radiopaque markers 22 can be positioned in a column around the tack. The distance "L" from the distal end of the tack to the radiopaque marker 22 can be the same as the distance from the distal end 52 of the outer sheath 12 to the radiopaque annular marker band 28. In some embodiments, this distance is to the center of the markers 22 and marker band 28. In some embodiments, the length "L" on the outer sheath is at least as long as the length "L" on the tack, if not slightly longer. The outer sheath can be free from other radiopaque markers. In addition, the tack can also be free from other radiopaque markers or columns of radiopaque markers. Thus, the outer sheath can have only a single marker band 28 at the distal end that is spaced from the distal-most end 52 of the outer sheath 12 by at least a distance from the distal-most end of the tack 2 to a radiopaque marker 22 or column of radiopaque markers. In the illustrated embodiment, the radiopaque marker 22 or column of radiopaque markers are positioned in the middle of the device. The radiopaque markers are also positioned on bridge members 18 that connect adjacent rings of undulating struts 16. In some embodiments, the radiopaque marker 22 or column of radiopaque markers can be spaced from the distal-most end of the tack by at least one ring of undulating struts 16. In the illustrated embodiment, the radiopaque marker 22 or column of radiopaque markers is not at the distal-most end of the tack 2, but is spaced therefrom.

Having corresponding radiopaque markers 22, 28 on the tack and the outer sheath can allow the physician to align the markers 22, 28 prior to deployment of the tack. Further, the physician can align the aligned markers with the desired area to be treated. As will be understood, all of this alignment can be done using standard visualization techniques. As has been mentioned, the annular pusher bands 44 on the inner shaft can also be radiopaque. In some embodiments, the pusher bands 44 can be identical and can appear different under visualization than both the marker on the outer sheath and the marker on the tack. Thus, it can be clear to the physician where all of the markers are and which is which. For example, the pusher bands 44 can be axially longer than the marker 28 on the outer sheath and the marker on the tack. Further, the markers on the delivery device can be bands, while the marker(s) on the tack can be dots.

Figure 7B:
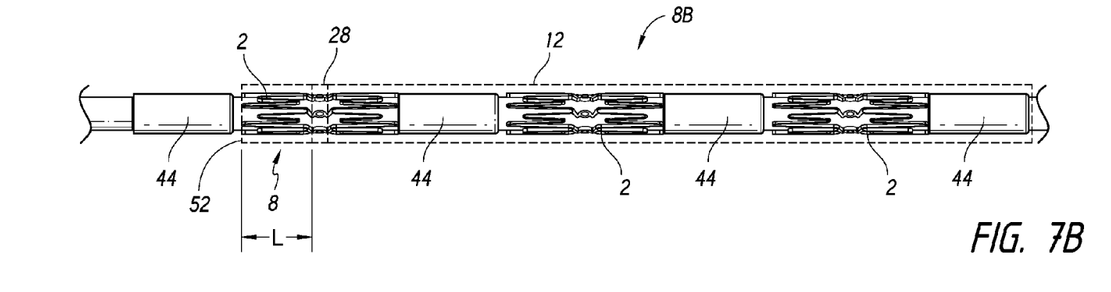

Looking to FIG. 7B, it can be seen that the marker 28 on the outer sheath 12 and the markers 22 on the first tack 2 are aligned and that the distal end of the sheath is positioned at the distal end of the first tack. The delivery device can now be positioned with respect to the lesion for treatment, such as by centering the radiopaque markers at desired location. The sheath can then be withdrawn to place the tack in the desired location.

In some embodiments, the delivery device can have a marker band on the outer sheath positioned proximally from the distal end-one at least half the length of the tack, the tack having a single column of markers at the middle of the device. A method of deployment can include withdrawing the outer sheath until the marker on the outer sheath and the tack to be delivered are aligned, and then aligning these two markers with the middle of the lesion to be treated (or other treatment area) before release of the tack, the release being affected by further withdrawing the outer sheath. It will be understood that markers on the pusher bands 44 can also be used to help align the delivery device before deployment.

Figure 7C:
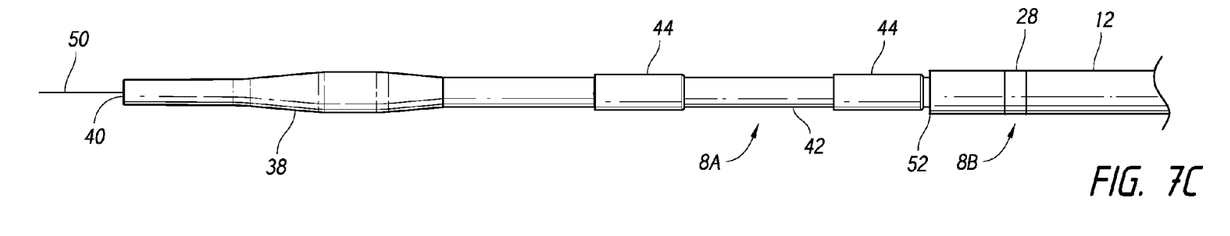

The method can be repeated to deliver multiple tacks (see FIG. 7C with tack shown in the compressed state for reference only). In between tack deployment, the delivery device may be moved to a completely different lesion or treatment area, or simply repositioned to ensure space between adjacent tacks once placed.

As discussed previously, in some embodiments, simultaneous placement of the entire tack can result upon release of the tack from the delivery device. Further, multiple tacks can placed as desired in a distal to proximal placement within the treatment segment of the vessel.

In some embodiments an expandable tack, such as that shown in FIGS. 3 & 3A, can exert a relatively constant force to a wide range of vessel lumen diameters, thereby allowing a single delivery catheter to deploy multiple tacks to varying sized vessels. Ideally the tack can be designed to treat vessels ranging in size from 2 to 8 mm, although other sized tacks could be delivered. It is desirable that the force applied by the tack to the vessel varies 5N or less over a 3 mm expansion range. More ideally the force applied will vary 1.5N or less over a 3 mm expansion range.

There are instances where drug coated balloons are being used as an alternative to placing a stent in the vessel. The balloon can dilate narrowing in the vessel and the drug helps to minimize post inflation inflammatory response which can lead to a re-narrowing of the artery. There is clinical evidence that the combination of a balloon and drug can provide an alternative to the implantation of a typical stent which have been historically used to provide both short term and long term scaffolding. Drug coated balloons are desirable in that there is no long term implant placed in the vessel. There are instances however when the expansion of a drug coated balloon may cause damage to the vessel in the form of a tissue dissection in which case a flap or piece of tissue extends into the lumen of the vessel. The dissection can occur within the balloon treatment zone as well as outside of or adjacent to the treatment zone. In these instances it is helpful to tack the dissected tissue against the arterial wall. A tack having a low outward force can beneficially be used to treat the dissection where a stent may not be appropriate, or desirable.

In some embodiments, the precise placement of the tack can be set upon positioning of the catheter within the vessel based on the position of a marker. Once positioned, one or more tacks can then be deployed while maintaining the catheter in place and slowly removing the outer sheath.

In some embodiments, one or more tacks can be deployed at a dissection of tissue. When an angioplasty procedure is performed there are typically one of three outcomes: 1) an optimal outcome, no further stenting or over treatment needs to be performed, 2) residual stenosis, usually requiring the placement of a stent to prop open or scaffold the vessel so that it remains open and does not return to the prior occluded or partially occluded state, and 3) a tissue dissection. A tissue dissection can be where the vessel experiences trauma such as the disruption of an arterial wall resulting in separation of the intimal layer. This may or may not be flow limiting. One or more tacks can beneficially be deployed at such a tissue dissection. Small tacks allow for the treatment of a subset of the portion of the blood vessel treated by the balloon angioplasty procedure thereby providing a treatment therapy with does not require the implantation of long metal stents over the entire angioplasty treatment area. Ideally, one or more tacks could be used to treat 60% or less of the length of vessel in the angioplasty treatment area. Small tacks having a single (illustrated) or double column of cells, have been shown to cause less injury and to have shorter recovery times than commonly available stents in treating tissue dissections.

Upon placement of the tack, an intravascular construct is formed in situ. The in situ placement can be in any suitable vessel, such as in any peripheral artery. The construct need not be limited to just two tacks. In fact, a plurality of at least three intravascular tacks can be provided in an intravascular construct formed in situ. In one embodiment each tack has a length of no more than about 8 mm, e.g., about 6 mm in an uncompressed state. In one configuration, at least one of, e.g., each of, the tacks are spaced apart from an adjacent tack by at least about 4 mm, or between about 4 mm and 8 mm or between about 6 mm and 8 mm. Although certain embodiments have a length of 8 mm or less, other embodiments can be longer, e.g., up to about 12 or 15 mm long. Also, neighboring tacks can be positioned as close as 2 mm apart, particularly in vessels that are less prone to bending or other movements. In some embodiments, a delivery device can be preloaded with six tacks, each about 6.5 mm long, and can be used to treat lesions up to 15 cm in length.

In the various delivery devices described herein, the spacing between implanted tacks can be controlled to maintain a set or a minimum distance between each tack. As can be seen, the delivery devices and/or tacks can include features that help maintain the desired distance between tacks. Maintaining proper inter-tack spacing can help ensure that the tacks are distributed over a desired length without contacting each other or bunching up in a certain region of the treated vessel. This can help to prevent kinking of the vessel in which they are disposed.

While a three tack construct formed in situ may be suitable for certain indications, an intravascular construct having at least 5 intravascular tacks may be advantageous for treating loose plaque, vessel flaps, dissections or other maladies that are significantly more elongated (non-focal). For example, while most dissections are focal (e.g., axially short), a series of dissections may be considered and treated as a more elongated malady.

In some cases, even shorter axial length tacks can be used to treat even more spaced apart locations. For example, a plurality of tacks, each having a length of no more than about 7 mm, can be placed in a vessel to treat a tackable malady. At least some of the tacks can be spaced apart from an adjacent tack by at least about 5 mm. In some cases, it may be preferred to provide gaps between adjacent tacks that can range from about 6 mm to about 10 mm.

Optionally, once the tacks are in place, the angioplasty balloon can be returned to the treatment site and inflated to expand the tacks to the desired state of expansion.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. An intraluminal device deployment method comprising:
    advancing a delivery device with a plurality of intraluminal devices in a compressed state to a treatment area, each of the plurality of intraluminal devices comprising a plurality of struts and a radiopaque marker positioned in a central region of the intraluminal device, each of the plurality of intraluminal devices being a same size with the radiopaque marker positioned in a same location,
    the delivery device comprising an inner shaft having a plurality of delivery platforms, each intraluminal device of the plurality of intraluminal devices positioned at a respective delivery platform of the plurality of delivery platforms, and an outer sheath covering the inner shaft and the plurality of delivery platforms, the outer sheath having a radiopaque marker band positioned proximally from a distal end of the outer sheath;
    withdrawing the outer sheath until the radiopaque marker band on the outer sheath and radiopaque marker on an intraluminal device to be delivered of the plurality of intraluminal devices are aligned such that a position of the radiopaque marker band on the outer sheath and a position of the radiopaque marker on the intraluminal device to be delivered of the plurality of intraluminal devices are longitudinally aligned along a longitudinal axis of the delivery device;
    aligning the aligned radiopaque marker band and the radiopaque marker with the treatment area before release of the intraluminal device such that the aligned radiopaque marker band and the radiopaque marker are longitudinally positioned with respect to the treatment area;
    withdrawing the outer sheath to release the intraluminal device; and
    withdrawing the outer sheath until the radiopaque marker band on the outer sheath and radiopaque marker on another intraluminal device to be delivered of the plurality of intraluminal devices are aligned.

2. The method of claim 1, wherein aligning the aligned radiopaque marker band and the radiopaque marker with the treatment area comprises centering the aligned radiopaque marker band and the radiopaque marker at a tissue dissection before release of the intraluminal device.

3. The method of claim 1, wherein withdrawing the outer sheath until the radiopaque marker band on the outer sheath and radiopaque marker on the intraluminal device to be delivered of the plurality of intraluminal devices are aligned comprises withdrawing the outer sheath until a distal-most end of the outer sheath and a distal-most end of the intraluminal device are aligned.

4. The method of claim 1, wherein withdrawing the outer sheath until the radiopaque marker band on the outer sheath and radiopaque marker on the intraluminal device to be delivered of the plurality of intraluminal devices are aligned comprises withdrawing the outer sheath until the radiopaque marker band is positioned at a middle of the intraluminal device.

5. The method of claim 1, wherein the intraluminal device has a single column of radiopaque markers comprising the radiopaque marker and withdrawing the outer sheath until the radiopaque marker band on the outer sheath and radiopaque marker on the intraluminal device to be delivered of the plurality of intraluminal devices are aligned comprises withdrawing the outer sheath until the radiopaque marker band encircles the single column of radiopaque markers.

6. The method of claim 1, further comprising advancing a guidewire to the treatment area, wherein the delivery device further comprises a guidewire lumen that extends through the inner shaft, the guidewire lumen being configured for receipt and advancement of a guidewire therein.

7. The method of claim 6, wherein advancing the delivery device to the treatment area comprises advancing the delivery device over the guidewire.

8. The method of claim 1, further comprising:
    advancing an angioplasty balloon to the treatment area prior to advancing the delivery device to the treatment area; and
    inflating the angioplasty balloon at the treatment area.

9. The method of claim 1, further comprising:
    advancing the delivery device to a second treatment area; and
    further withdrawing the outer sheath to release another intraluminal device of the plurality of intraluminal devices.

10. The method of claim 1, wherein each of the plurality of delivery platforms comprises a recess extending between a pair of annular pusher bands, the annular pusher bands being radiopaque, wherein the annular pusher bands appear different under visualization than both the radiopaque marker band on the outer sheath and radiopaque marker on each of the intraluminal devices of the plurality of intraluminal devices.

11. The method of claim 1, further comprising unscrewing a tuohy borst adapter of the delivery device to release the inner shaft from a locking relationship with the outer sheath prior to withdrawing the outer sheath until the radiopaque marker band on the outer sheath and radiopaque marker on the intraluminal device to be delivered of the plurality of intraluminal devices are aligned.

12. An intraluminal device deployment method comprising:
advancing a delivery device to a treatment area, the delivery device comprising:
an inner shaft; and
a plurality of delivery platforms, a self-expanding medical device with a radiopaque marker, of a plurality of self-expanding medical devices, positioned around each of the delivery platforms, each delivery platform comprising:
a pair of fixed annular bands around the inner shaft; and
a sleeve secured to the inner shaft and positioned between the inner bands; and
an outer sheath configured to extend over the plurality of self-expanding medical devices to maintain each of the plurality of self-expanding medical device in a compressed state, the outer sheath having a radiopaque marker band positioned proximally from a distal end of the outer sheath;
aligning along a longitudinal axis of the delivery device the radiopaque marker band on the outer sheath with the radiopaque marker on a self-expanding medical device of the plurality of self-expanding medical devices;
positioning the aligned radiopaque marker band and the radiopaque marker longitudinally with respect to the treatment area; and
withdrawing the outer sheath to release the self-expanding medical device.

13. The method of claim 12, wherein aligning the aligned radiopaque marker band and the radiopaque marker with the treatment area comprises centering the aligned radiopaque marker band and the radiopaque marker at a tissue dissection before release of the self-expanding medical device.

14. The method of claim 12, wherein aligning the radiopaque marker band on the outer sheath and the radiopaque marker on the self-expanding medical device comprises withdrawing the outer sheath until a distal-most end of the outer sheath is aligned with a corresponding distal-most end of the self-expanding medical device.

15. The method of claim 12, wherein aligning the radiopaque marker band on the outer sheath and the radiopaque marker on the self-expanding medical device comprises withdrawing the outer sheath until the radiopaque marker band is positioned at a middle of the self-expanding medical device.

16. The method of claim 12, wherein the self-expanding medical device has a single column of radiopaque markers and aligning the radiopaque marker band on the outer sheath and the radiopaque marker on the self-expanding medical device comprises withdrawing the outer sheath until the radiopaque marker band encircles the single column of radiopaque markers.

17. The method of claim 12, wherein the delivery device further comprises a plurality of additional delivery platforms for sequential delivery of the plurality of self-expanding medical devices.

18. The method of claim 12, further comprising:
advancing an angioplasty balloon to the treatment area prior to advancing the delivery device to the treatment area; and
inflating the angioplasty balloon at the treatment area.

19. The method of claim 12, further comprising:
advancing the delivery device to a second treatment area; and
further withdrawing the outer sheath to release another self-expanding medical device of the plurality of self-expanding medical devices.

20. The method of claim 12, wherein each of the plurality of delivery platforms comprises a recess extending between a pair of annular pusher bands, the annular pusher bands being radiopaque, wherein the annular pusher bands appear different under visualization than both the radiopaque marker band on the outer sheath and radiopaque marker on each of the self-expanding medical devices of the plurality of self-expanding medical devices.

21. An intraluminal device deployment method comprising:
advancing a delivery device with a plurality of intraluminal devices in a compressed state to a treatment area, each of the plurality of intraluminal devices comprising a plurality of struts and a radiopaque marker positioned in a central region of the intraluminal device, the delivery device comprising an inner shaft having a plurality of delivery platforms, each intraluminal device of the plurality of intraluminal devices positioned at a respective delivery platform of the plurality of delivery platforms, and an outer sheath covering the inner shaft and the plurality of delivery platforms, the outer sheath having a radiopaque marker band positioned proximally from a distal end of the outer sheath;
withdrawing the outer sheath until the radiopaque marker band on the outer sheath and radiopaque marker on a intraluminal device to be delivered of the plurality of intraluminal devices are aligned along a longitudinal axis of the delivery device;
longitudinally aligning the aligned radiopaque marker band and the radiopaque marker with the treatment area before release of the intraluminal device;
withdrawing the outer sheath to release the intraluminal device; and
withdrawing the outer sheath until the radiopaque marker band on the outer sheath and radiopaque marker on another intraluminal device to be delivered of the plurality of intraluminal devices are aligned.

22. The method of claim 21, wherein aligning the aligned radiopaque marker band and the radiopaque marker with the treatment area comprises centering the aligned radiopaque marker band and the radiopaque marker at a tissue dissection before release of the intraluminal device.

23. The method of claim 21, wherein withdrawing the outer sheath until the radiopaque marker band on the outer sheath and radiopaque marker on the intraluminal device to be delivered of the plurality of intraluminal devices are aligned comprises withdrawing the outer sheath until a distal-most end of the outer sheath and a distal-most end of the intraluminal device are aligned.

24. The method of claim 21, wherein withdrawing the outer sheath until the radiopaque marker band on the outer sheath and radiopaque marker on the intraluminal device to be delivered of the plurality of intraluminal devices are aligned comprises withdrawing the outer sheath until the radiopaque marker band is positioned at a middle of the intraluminal device.

25. The method of claim 21, wherein the intraluminal device has a single column of radiopaque markers comprising the radiopaque marker and withdrawing the outer sheath until the radiopaque marker band on the outer sheath and radiopaque marker on the intraluminal device to be delivered of the plurality of intraluminal devices are aligned comprises withdrawing the outer sheath until the radiopaque marker band encircles the single column of radiopaque markers.

* * * * *